US00PP29135P2

(12) United States Plant Patent
Hoogendoorn

(10) Patent No.: US PP29,135 P2
(45) Date of Patent: Mar. 20, 2018

(54) ***MILTONIDIUM* ORCHID PLANT NAMED 'CAMBLAJE'**

(50) Latin Name: *Nothogenus:×Miltonidium*
Varietal Denomination: CAMBLAJE

(71) Applicant: ANTHURA B.V., Bleiswijk (NL)

(72) Inventor: Gert-Jan Hoogendoorn, Woubrugge (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 15/530,426

(22) Filed: Jan. 12, 2017

(51) Int. Cl.
*A01H 5/02* (2006.01)

(52) U.S. Cl.
USPC ..... Plt./311

(58) Field of Classification Search
USPC ..... Plt./311
See application file for complete search history.

(56) References Cited

PUBLICATIONS

PLUTO Plant Variety Database Dec. 8, 2017. p. 1.*

* cited by examiner

*Primary Examiner* — Annette H Para
(74) *Attorney, Agent, or Firm* — Jondle & Associates, P.C.

(57) ABSTRACT

A new and distinct variety of ×*Miltonidium* plant named 'CAMBLAJE', particularly characterized by having dark red flowers with a large dark red, light pink and white lip, 1-3 peduncles, a peduncle that is long and sturdy, leaves that are lanceolate and elongated to very elongated, and is propagated by meristem tissue culture is disclosed.

3 Drawing Sheets

Genus and species: *Nothogenus:×Miltonidium.*
Variety denomination: 'CAMBLAJE'.

BACKGROUND OF THE NEW PLANT

The present invention comprises a new and distinct cultivar of ×*Miltonidium* plant, botanically known as ×*Miltonidium* of the Orchidaceae family, and hereinafter referred to by the cultivar name 'CAMBLAJE'.

Miltonia, Odontoglossum, *Oncidium* and Brassia and some other genera are a complex group of orchid species that are easily hybridized. The boundaries between the genera have been under discussion for the last several decades. According to the most recent classification by Pridgeon, Cribb, Chase and Rasmussen (Genera Orchidacearum), the plant herein described is most likely a complex hybrid between Miltonia and *Oncidium* species, hence called a ×*Miltonidium.*

All ×*Miltonidium* plants exhibit a sympodial growth habit. The species typically have 4 to 6 leaves per mature pseudobulb: most of the time one lanceolate leaf with an acute apex grown on the apex of the pseudobulb and four leaves grown from the axis at the base (sympodial growth); two leaves on each side. The peduncles vary in size from 20-90 cm.

×*Miltonidium* orchids are used as flowering potted-plants for home or interiorscape. ×*Miltonidium* produces upright or pendent lateral racemes or panicles, often with many showy flowers which open in succession beginning with the lowermost. The flowers possess three sepals and two petals; the lateral ones being alike and a peculiar labellum. Flower colors include various shades of pink, white, yellow, and red-brown.

×*Miltonidium* orchids are typically propagated from tissue culture. Asexual propagation of ×*Miltonidium* is often done from off-shoots which arise from the lower bracts of the inflorescence. The resulting plants are detached from the mother plants and may be planted in a suitable substrate.

The new ×*Miltonidium* 'CAMBLAJE' is particularly characterized by its attractive and unique dark red flowers with a large dark red, light pink and white lip, economical propagation by tissue culture, early flowering, and a plant dimension suitable for packaging and shipping to the market.

'CAMBLAJE' is a product of a planned breeding program conducted by the inventor in Bleiswijk, The Netherlands.

The new ×*Miltonidium* 'CAMBLAJE' originated from a cross made by the inventor in July 2004 in Bleiswijk, The Netherlands. The female parent is a red-brown ×*Miltonidium* pot plant named '60000-0081' (unpatented) and the male parent is a brown-green *Oncidium* pot plant named '60000-0061' (unpatented). A single plant was selected by the inventor from within the progeny of the stated cross-pollination in a controlled greenhouse in Bleiswijk, The Netherlands in April 2008.

Asexual reproduction of 'CAMBLAJE' by meristem tissue culture since 2010 in Bleiswijk, The Netherlands has demonstrated that the new variety reproduces true to type with all of the characteristics, as herein described, firmly fixed and retained through successive generations.

Plant Breeder's Rights for this variety have been applied for in Europe on Mar. 18, 2016. 'CAMBLAJE' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in Bleiswijk, The Netherlands.

1) Dark red flower with a large dark red, light pink and white lip;
2) 1-3 peduncles;
3) Peduncle is long and sturdy;
4) The shape of the leaf is lanceolate and is elongated to very elongated; and
5) Plants are propagated by meristem tissue culture.

DESCRIPTION OF THE PHOTOGRAPHS

This new ×*Miltonidium* plant is illustrated by the accompanying photographs which show the overall plant habit including blooms, buds and foliage of the plant; the colors shown are as true as can be reasonably obtained by conventional photographic procedures. The photographs are of a 70-week old plant grown in a greenhouse in Bleiswijk, The Netherlands in November 2016.

DESCRIPTION OF THE NEW VARIETY

Figure 1:
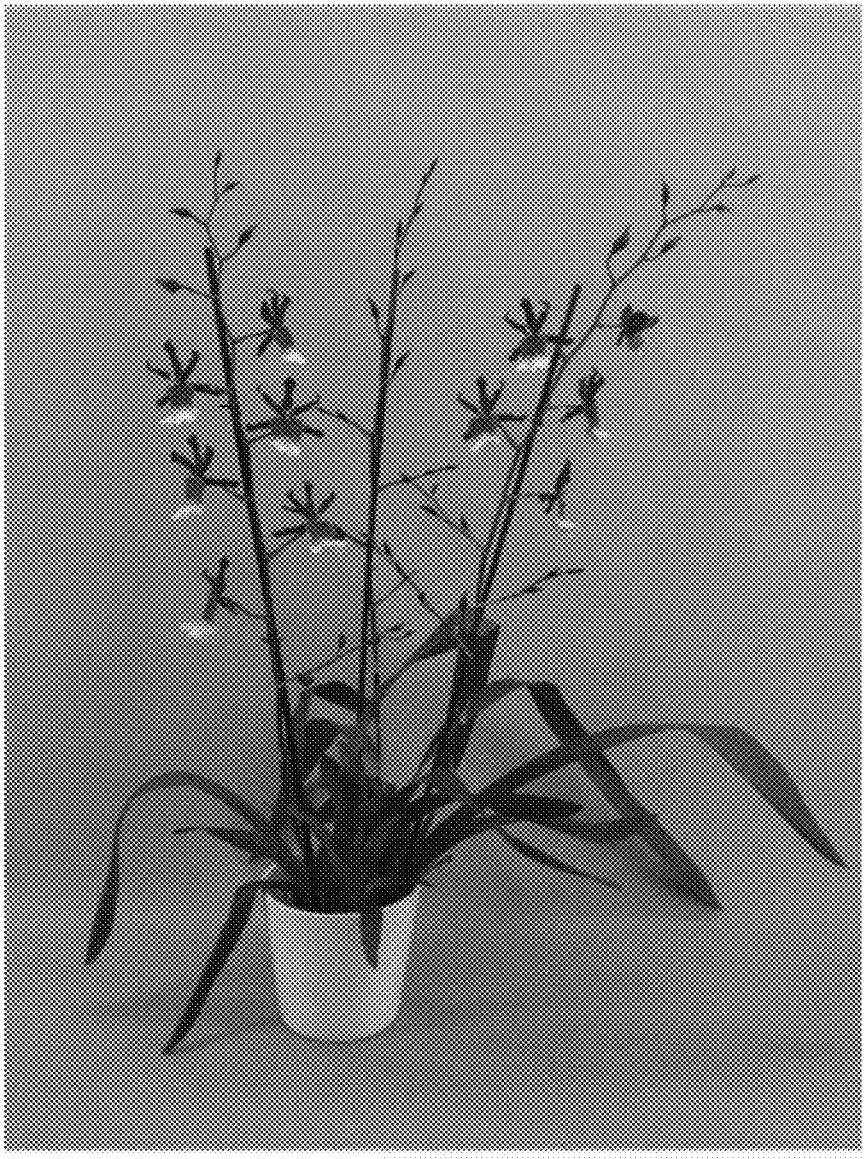
FIG. 1 shows the overall plant habit, including blooms, buds and foliage of 'CAMBLAJE'.
Figure 2:
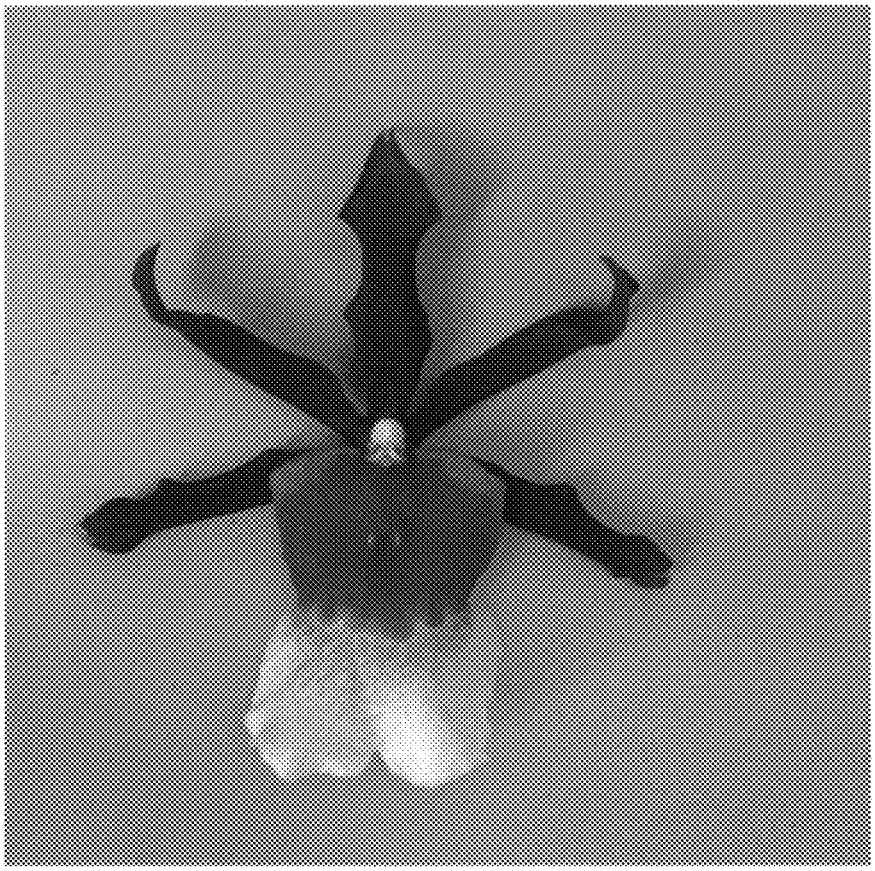
FIG. 2 shows a close-up of a flower of 'CAMBLAJE'.
Figure 3:
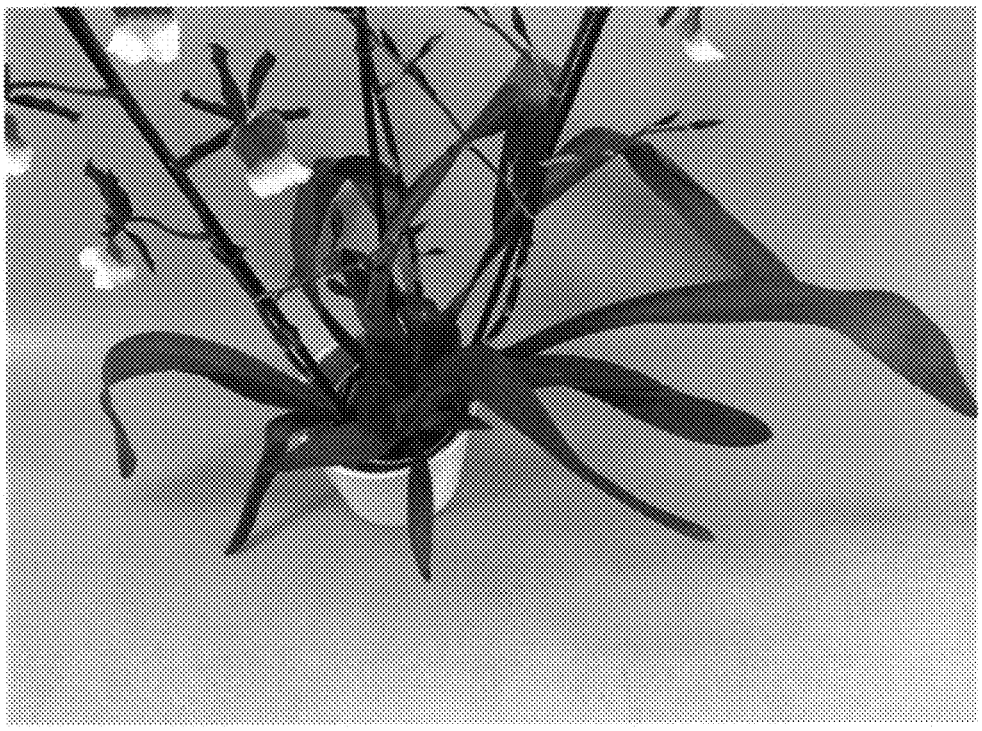
FIG. 3 shows a top view of the leaves of 'CAMBLAJE'.

The following detailed description sets forth the distinctive characteristics of 'CAMBLAJE'. The data which define these characteristics were collected from asexual reproductions carried out in Bleiswijk, The Netherlands. The plant history was taken on 70-week old plants which were planted from tissue culture in 12 centimeter pots and grown in a greenhouse between 20° C. to 25° C. for 50 to 70 weeks. Observations were made in November 2016. Color readings were taken under 4000-6000 lux natural light in the greenhouse. Color references are primarily to The R.H.S. Colour Chart of The Royal Horticultural Society of London (R.H.S.) (2015).

DETAILED BOTANICAL DESCRIPTION

Classification:
- *Family*.—Orchidaceae.
- *Botanical*.—×*Miltonidium*.
- *Common name*.—Cambria.
- *Variety name*.—'CAMBLAJE'.

Parentage:
- *Female parent*.—×*Miltonidium* cultivar '60000-0081' (unpatented).
- *Male parent*.—*Oncidium* cultivar '60000-0061' (unpatented).

Propagation:
- *Type*.—Tissue culture.

Plant:
- *Crop time* (*time to produce a finished flowering plant*).—50 to 70 weeks for a 12 cm pot.
- *Growth habit of peduncle*.—Standard, green leaves, panicle.
- *Height* (*including pot, including inflorescence*).—75.0 cm to 85.0 cm.
- *Width* (*measured from leaf tips*).—40.0 cm to 50.0 cm.
- *Vigor*.—Moderate.

Roots:
- *Root description*.—Greyed-yellow (RHS 162A) colored roots lightly branching with light growing tips (RHS 161B) (The exact shades of white may vary with minimal changes of environmental conditions).

Pseudobulb:
- *Number of pseudobulbs*.—1 to 3.
- *Shape*.—Laterally compressed ovoid.
- *Length*.—8.0 cm to 9.0 cm.
- *Width*.—5.0 cm to 6.0 cm.
- *Thickness*.—1.5 cm to 2.0 cm.
- *Color*.—Green (RHS 146A).

Leaves:
- *Mature leaves*.—Quantity per pseudobulb: 4 to 6 leaves are produced before flowering. Length (fully expanded): 30.0 cm to 35.0 cm. Width: 4.0 cm to 4.5 cm. Shape: Lanceolate. Base shape: Elongated to very elongated. Apex: Acute. Leaf margin: Entire. Color: Upper surface: RHS 146A. Lower surface: RHS 146B. Texture: Upper surface: Smooth. Lower surface: Smooth. Thickness: 0.45 mm to 0.50 mm. Venation: Pattern: Parallel. Color of the midvein: Upper surface: RHS 146A. Lower surface: RHS 146B.

Peduncle:
- *Quantity per plant*.—1 to 3.
- *Number of flowers per peduncle*.—14 to 24.
- *Length*.—From 64.0 cm to 74.0 cm.
- *Diameter*.—5.3 mm to 6.3 mm.
- *Strength*.—Strong.
- *Aspect*.—Upright.
- *Texture*.—Smooth.
- *Color*.—Mix of green (RHS 146C) and brown (RHS N199B).
- *Internode length*.—65.0 mm to 70.0 mm.
- *Number of branches*.—1 to 4.
- *Callosities*.—None.

Inflorescence description:
- *Appearance*.—Upright, panicle inflorescence with bilaterally symmetrical flowers that open in succession beginning with the lowermost flower.
- *Inflorescence size*.—Height (from base to tip): 430.0 mm to 480.0 mm.
- *Flowering time*.—First flowers can be expected 4 to 6 months after planting in a 12 cm pot.
- *Flower*.—Height: 71.0 mm to 76.0 mm. Diameter: 67.0 mm to 73.0 mm.
- *Flower longevity*.—On the plant: 4 to 6 weeks.
- *Fragrance*.—Present.
- *Petals*.—Shape: Elliptic. Apex: Acute. Margin: Undulated. Length (from base to tip): 35.0 mm to 37.0 mm. Width: 12.0 mm to 14.0 mm. Color (when fully opened): Upper surface: Basic color: Dark red (RHS 187A). Over color: Dark red tips and at the base (RHS 187C). Lower surface: Basic color: Dark red (RHS 187C). Over color: Dark red edges (RHS 187A).
- *Dorsal sepal*.—Shape: Elliptic. Apex: Acute. Margin: Undulated. Length (from base to tip): 34.0 mm to 36.0 mm. Width: 11.0 mm to 13.0 mm. Color (when fully opened): Upper surface: Basic color: Dark red (RHS 187A). Over color: Dark red tips (RHS 187C). Lower surface: Basic color: Dark red (RHS 187A). Over color: Light greyed-green in the middle (RHS 195C).
- *Lateral sepals*.—Shape: Elliptic. Margin: Undulated. Length (from base to tip): 37.0 mm to 39.0 mm. Width: 10.0 mm to 12.0 mm. Color (when fully opened): Upper surface: Basic color: Dark red (RHS 187A). Over color: Dark red tips (RHS 187C).

Lower surface: Basic color: Light greyed-green (RHS 195C). Over color: Dark red edges (RHS 187A).

*Labellum* (*lip*).—Length: 35.0 mm to 37.0 mm. Width: 36.0 mm to 38.0 mm. Color: Upper surface: Dark red (RHS 187C and 59A), light pink towards the edge (RHS 186C) and white (RHS NN155C). Lower surface: Pink (RHS 186C) with dark red fleck (RHS 187D) and white (RHS NN155C) towards the edge. Margin: Undulated.

*Callus*.—Color: Dark red (RHS 185A) with yellow tips (RHS 11A). Shape: Indescribable. Average size: Indescribable. Average number of protuberance: 3 to 5.

Reproductive organs:

*Arrangement*.—The stamens, style and stigmas are fused into a single, short structure called the column, possessing one terminal anther with pollen grains united into pollinia, which are covered by an anther cap. The stigma is located under the column behind the pollinia. The ovary is inferior with three carpels present.

*Column*.—Length: 7.0 mm to 9.0 mm. Diameter: 3.8 mm to 4.3 mm. Color: Dark red (RHS 187B). Wings: Absent.

*Cap*.—Average size: 1.0 mm to 3.0 mm. Shape: Oval cup shape. Color: White (RHS NN155C).

*Pollinia*.—Quantity: 2. Diameter: 0.3 mm to 0.5 mm. Color: Yellow-orange (RHS 14A).

*Ovary*.—Length: 14.0 mm to 16.0 mm. Diameter: 1.9 mm to 2.1 mm.

*Pedicel*.—Length: 42.0 mm to 44.0 mm. Diameter: 2.2 mm to 2.5 mm. Color: Dark red (RHS 187B); lighter red towards the flower (RHS 187A).

Disease, pest, and stress resistance: No specific resistance or susceptibility observed.

Temperature tolerance: Not observed.

COMPARISON WITH PARENTAL AND SIMILAR COMMERCIAL VARIETIES

'CAMBLAJE' differs from female parent '60000-0081' (unpatented) in that 'CAMBLAJE' has narrow dorsal and lateral sepal widths and a dark red, light pink and white lip, whereas '60000-0081' has broad dorsal and lateral sepal widths and a moderate red and white lip.

'CAMBLAJE' differs from male parent '60000-0061' (unpatented) in that 'CAMBLAJE' has dark red flowers with an even pattern, whereas '60000-0061' has brown and green flowers with a striped pattern.

'CAMBLAJE' is most similar to the commercial ×*Burrageara* plant named 'CAMBOPAL' (unpatented) and a ×*Miltonidium* plant named 'CAMBOLYK' (U.S. Plant patent application Ser. No. 14/545,659). 'CAMBLAJE' differs from commercial variety 'CAMBOPAL' in that 'CAMBLAJE' has a dark red, light pink and white lip, whereas 'CAMBOPAL' has a purple lip with white irregular spots and half dark purple-red at the base. Additionally, 'CAMBLAJE' has a larger flower diameter and a wider lip than 'CAMBOPAL'.

'CAMBLAJE' differs from commercial variety 'CAMBOLYK' in that 'CAMBLAJE' has a dark red, light pink and white lip, whereas 'CAMBOLYK' has a purple lip that is somewhat darker, bluer towards the margin, with white irregular spots. Additionally, 'CAMBLAJE' has a larger flower diameter and a wider lip than 'CAMBOLYK'.

I claim:

1. A new and distinct variety of ×*Miltonidium* plant named 'CAMBLAJE', substantially as described and illustrated herein.

* * * * *